(12) United States Patent
Webb (10) Patent No.: US 7,377,410 B1
(45) Date of Patent: May 27, 2008

(54) METHOD AND APPARATUS FOR DONNING GARMENTS

(76) Inventor: Paul Paine Webb, 370 Orton Rd., Yellow Springs, OH (US) 45387

( * ) Notice: Subject to any disclaimer, the term of this patent is extended or adjusted under 35 U.S.C. 154(b) by 504 days.

(21) Appl. No.: 11/032,624

(22) Filed: Jan. 10, 2005

(51) Int. Cl.
*A47G 25/80* (2006.01)

(52) U.S. Cl. .................................................. 223/111

(58) Field of Classification Search .............. 223/1, 223/111–119
See application file for complete search history.

(56) References Cited

U.S. PATENT DOCUMENTS

| | | | |
|---|---|---|---|
| 882,312 A | 3/1908 | Hoefftcke | |
| 1,938,685 A | 12/1933 | Bruels et al. | |
| 1,996,377 A | 4/1935 | Hinchen | |
| 2,741,410 A | 4/1956 | Violette | |
| 3,049,896 A | 8/1962 | Webb | |
| 3,067,001 A | 12/1962 | McCollum | |
| 3,103,016 A | 9/1963 | Perlman | |
| 3,337,279 A | 8/1967 | Reinhardt et al. | |
| 3,401,683 A | 9/1968 | Webb et al. | |
| 3,695,493 A | 10/1972 | Karr | |
| 4,069,913 A | 1/1978 | Harrigan | |
| 4,155,494 A | 5/1979 | Poncy et al. | |
| 4,708,272 A * | 11/1987 | Guerra | 223/113 |
| 4,915,272 A | 4/1990 | Vlock | |
| 5,058,785 A | 10/1991 | Rich et al. | |
| 5,078,308 A * | 1/1992 | Sullivan | 223/111 |
| 5,153,938 A | 10/1992 | Epperson | |
| 5,673,826 A * | 10/1997 | Stolk | 223/112 |
| 6,000,059 A | 12/1999 | Abts | |
| 6,021,935 A | 2/2000 | Yonezawa | |
| 6,032,839 A * | 3/2000 | Joosten et al. | 223/112 |
| 6,154,886 A | 12/2000 | Hottner | |
| 6,163,885 A | 12/2000 | Webb | |
| 6,360,373 B1 | 3/2002 | Rehn et al. | |
| 6,415,447 B1 | 7/2002 | Frazier | |
| 6,427,883 B1 | 8/2002 | Esten | |
| 6,430,750 B1 | 8/2002 | Tourbier et al. | |
| 6,430,751 B1 | 8/2002 | Tourbier et al. | |
| 6,435,388 B1 | 8/2002 | Binder et al. | |
| 6,523,729 B1 * | 2/2003 | Gardon-Mollard | 223/112 |

(Continued)

OTHER PUBLICATIONS

Paul Webb, M.D.; The Space Activity Suit: An Elastic Leotard for Extravehicular Activity; Aerospace Medicine; Apr. 1968; pp. 376-383; vol. 39, No. 4.

*Primary Examiner*—Gary L. Welch
*Assistant Examiner*—Andrew W Sutton
(74) *Attorney, Agent, or Firm*—Stevens & Showalter LLP (57) ABSTRACT

Systems, apparatuses and methods of donning garments are provided wherein an expandable layer is temporarily inserted into a garment. A source such as a donning chamber is utilized to expand the temporary expandable layer, thus stretching the garment by an amount suitable to assist the wearer in donning the garment. Once donned, the expandable layer is at least partially removed from underneath the garment. For example, pieces of the expandable layer may be pulled through a mesh fabric of the garment, or otherwise slipped out from under the garment. Alternatively, the temporary expandable layer may be constructed such that, at least portions are soluble. Once the garment is donned, the soluble portions of the temporary expandable layer are dissolved using a corresponding solvent. Still further, a physical treatment such as ultrasound or ultraviolet radiation, may be used to crumble or disintegrate a portion or the entire temporary expandable layer.

18 Claims, 5 Drawing Sheets

U.S. PATENT DOCUMENTS

| | | |
|---|---|---|
| 6,554,168 B2 | 4/2003 | Stobart |
| 2002/0116743 A1 | 8/2002 | Tourbier et al. |
| 2002/0116744 A1 | 8/2002 | Tourbier et al. |
| 2007/0119882 A1* | 5/2007 | Scott .................... 223/111 |

* cited by examiner

METHOD AND APPARATUS FOR DONNING GARMENTS

BACKGROUND OF THE INVENTION

The present invention relates in general to donning garments, and more particularly to methods, apparatuses and systems for donning compression, pressure and other forms of support garments including for example, mechanical counter pressure garments.

A mechanical counter pressure suit (MCP suit) comprises a carefully tailored set of elastic mesh garments including a full body leotard that covers the torso, arms, hands, legs and feet. Developed for use during extra-vehicular activity in the manned space flight programs of the National Aeronautics and Space Administration (NASA), the MCP suit is worn with a gas pressurized helmet and is designed to permit free circulation of blood in environments having very small or no ambient gas pressure, such as at high altitudes or the vacuum of space.

Gas must be delivered to the lungs at a pressure sufficient to ensure diffusion of oxygen into the blood to prevent the onset of hypoxia. In environments having very small or no ambient gas pressure, the gas-pressurized helmet of the MCP suit provides oxygen at a positive pressure, for example, at a pressure of approximately 4.3 pounds per square inch, or 222 millimeters of mercury (mmHg). However, blood pressure will rise correspondingly with a rise in the pressure of the breathing gas. If tissue pressure is not substantially matched to the increased blood pressure, then soft tissue can swell and blood can pool in low pressure areas resulting in edema and decreased circulating volume of blood. To compensate for the effects of positive pressure breathing, the MCP suit provides a mechanical counter pressure to the body that is intended to match the increased blood pressure caused by the pressure difference between the ambient pressure and the positive breathing pressure provided by the gas-pressurized helmet.

To perform the mechanical counter pressure function, the MCP suit is typically provided as a multi-piece, form fitted, full body restraint suit that takes into consideration the geometrical irregularities of the wearer. The MCP suit thus includes uniquely customized garments that cover the torso, arms, legs, hands and feet of the wearer. The torso portion comprises a leotard that is constructed of an elastic cloth, but may also include breathing bladders, non-elastic cloth, and one or more closure structures. The addition of closure structures, e.g., zippers, allows the torso component of the elastic leotard to be donned without significant impediment. However, no closure structure is typically provided for the MCP garments that are worn over the hands, arms, feet and legs. The absence of a closure structure combined with the pressure exerted on the body by a properly fitted mechanical counter pressure garment, makes the MCP suit, and in particular, the arm, leg, foot and hand garments difficult to don. Moreover, excessive and sustained tugging of the MCP garments may result in fatigue to the material, which may affect their mechanical counter pressure capabilities.

SUMMARY OF THE INVENTION

The present invention provides systems and methods of donning garments and is suitable for use in donning compression, pressure and other forms of support garments. A temporary expandable layer is inserted into a garment, such as mechanical counter pressure glove. A source such as a donning chamber is then utilized to expand or otherwise inflate the temporary expandable layer, thus expanding the garment by an amount suitable to assist the wearer in donning the garment. Once donned, the temporary expandable layer is at least partially removed from underneath the garment.

One exemplary approach to removing the temporary expandable layer is to provide cords extending from the temporary expandable layer that pass through the garment. The cords may be pulled, causing the temporary expandable layer to tear or otherwise separate into pieces that can be removed through the garment, or otherwise slipped out from under the garment. Alternatively, the temporary expandable layer may be constructed such that, at least portions are soluble. Once the garment is donned, the soluble portions of the temporary expandable layer are dissolved using a corresponding solvent. Still further, a physical treatment such as ultrasound or ultraviolet radiation, may be used to crumble or disintegrate at least a portion of the temporary expandable layer.

BRIEF DESCRIPTION OF THE SEVERAL VIEWS OF THE DRAWINGS

The following description of the preferred embodiments of the present invention can be best understood when read in conjunction with the following drawings, where like structure is indicated with like reference numerals, and in which.

DETAILED DESCRIPTION OF THE INVENTION

In the following description of the preferred embodiments, reference is made to the accompanying drawings that form a part hereof, and in which is shown by way of illustration, and not by way of limitation, specific preferred embodiments in which the invention may be practiced. It is to be understood that other embodiments may be utilized and that changes may be made without departing from the spirit and scope of the present invention.

It is difficult to don mechanical counter pressure garments, especially mechanical counter pressure gloves, due to the pressure (222 mmHg) that the mechanical counter pressure garment typically exerts on the wearer. Thus, for sake of clarity, the donning of mechanical counter pressure gloves, arm, feet and leg garments will be discussed herein. However, the systems, apparatuses and methods of the present invention are broadly applicable to donning pressure, compression and other forms of support garments, including for example, mechanical counter pressure garments, medical garments such as post surgery garments and anti-embolism garments, and generally, a wide variety of support garments.

Figure 1:
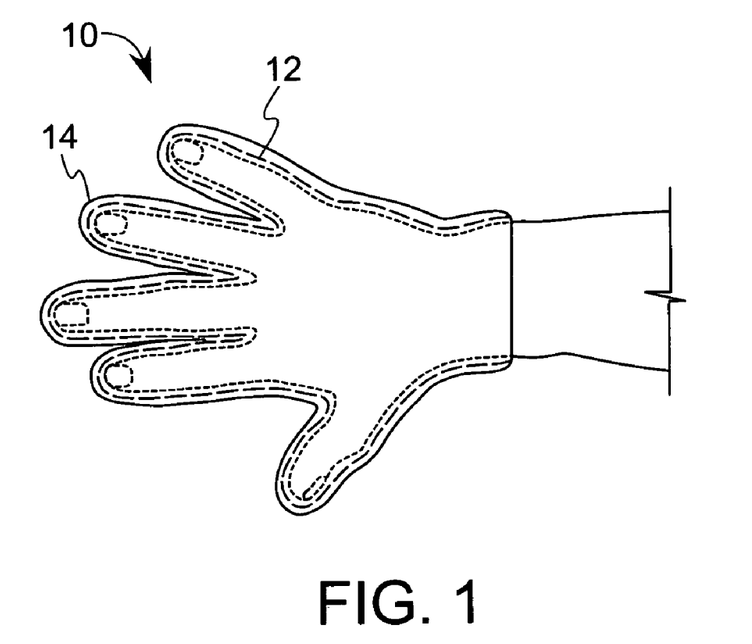
FIG. 1 illustrates an exemplary mechanical counter pressure glove.

Referring now to the drawings, and particularly to FIG. 1, a mechanical counter pressure glove 10 includes an innermost garment, which is referred to herein as a comfort layer 12, and an outermost garment, which is referred to herein as a power layer 14. The mechanical counter pressure glove 10 is typically worn as a component of a mechanical pressure suit, which also comprises a full body leotard that further covers the torso, arms, legs and feet of the wearer (complete suit not shown). The comfort layer 12 typically comprises a stretchable layer constructed from knitted nylon, polyester, or other suitable yarn that is woven with an elastomeric yarn so as to substantially conform to the shape of the hand. The comfort layer 12 applies little pressure and is provided as an intermediate layer between the soft tissue of the hand and the power layer 14. As such, the comfort layer 12 is donned with relative ease.

The power layer 14 is a main component in providing mechanical counter pressure to the hand. For example, depending upon the application, the power layer 14 may be required to apply pressure in the range of 200-220 mmHg against the hand when properly donned. In order to exert the necessary mechanical counter pressure, the power layer 14 is comprised of a strong, elastic material such as 1600 or greater denier elastomeric yarn that may be woven or knitted into a fabric matrix that includes cross fibers of non-elastic yarn. The need for a tight fit, which is required to exert the appropriate pressure, made donning the power layer 14 over the comfort layer 12 a tedious task prior to the present invention.

Depending upon the application, there may be additional layers between the comfort layer 12 and the power layer 14. For example, a slip layer (not shown) may be donned over the comfort layer 12 prior to donning the power layer 14. The slip layer may be constructed from, or treated with a friction reducing substance or material to assist the wearer in donning the power layer 14. For example, the slip layer may be constructed from polytetrafluoroethylene (PTFE) fiber and yarn. However, even with the aid of friction reducing intermediate layers, the power layer 14 may still be difficult to don. Further, bladders, springs and other pressure devices (not shown) may be provided between the comfort layer 12 and the power layer 14 to assist in providing mechanical counter pressure to the hand.

Figure 2:
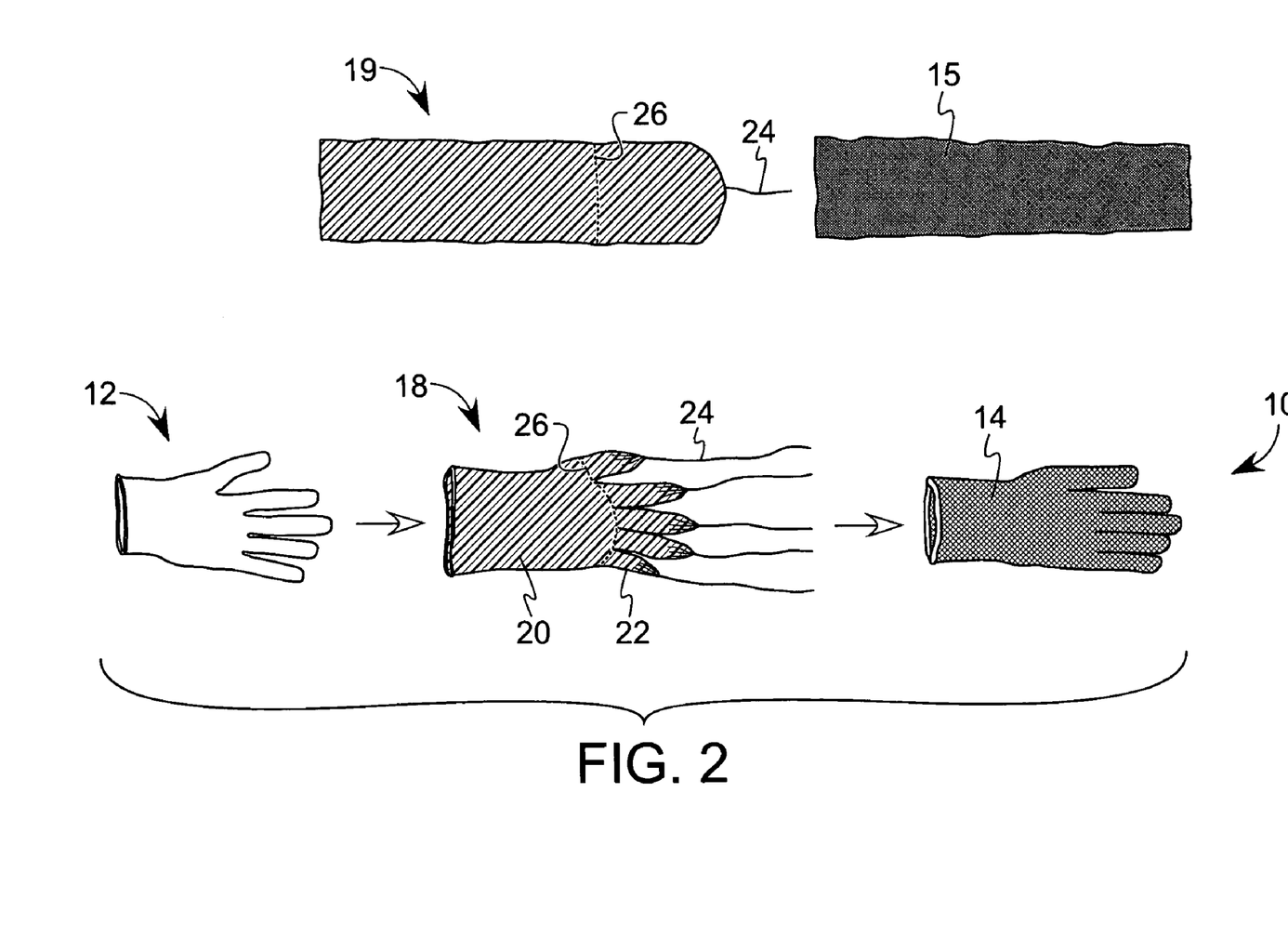
FIG. 2 illustrates a comfort layer, a temporary expandable layer and a power layer of a mechanical counter pressure glove and a temporary expandable layer shaped as a blind tube and a corresponding power layer, which may comprise an arm, leg, foot or similar garment.

Referring to FIG. 2, a temporary expandable layer 18 is provided to assist the wearer in donning the power layer 14. The temporary expandable layer 18 comprises for example, a stretchable nonporous or gas-tight material such as a plastic material, and is utilized to briefly expand the corresponding power layer 14 during at least a portion of the donning process. That is, the wearer dons the comfort layer 12 and any necessary intermediate layers and uses the temporary expandable layer 18 to briefly stretch the power layer 14 for donning. The temporary expandable layer 18 is not part of the mechanical counter pressure suit. As such, once the power layer 14 has been donned, the temporary expandable layer 18 is relaxed to a non-expanded state and is removed, at least partially, from underneath the power layer 14 as will be described in greater detail herein.

The temporary expandable layer 18 comprises generally, a palm portion 20 and a plurality of finger portions 22. As the temporary expandable layer 18 will be discarded after donning the power layer 14, the palm portion 20 and finger portions 22 need not be carefully shaped. The temporary expandable layer 18 may additionally include one or more cords 24 extending from each finger portion 22. The cords 24 can be made integral with the material of the temporary expandable layer 18, or may be otherwise attached to the finger portions 22 of the temporary expandable layer 18. Further, weakened areas 26 may be provided about the temporary expandable layer 18. As shown, weakened areas 26 are schematically represented by the dashed lines proximate to the area between a palm portion 20 and corresponding finger portions 22. The weakened areas 26 may comprise stretched, thinned, or otherwise weakened areas, cut lines or perforations, or other features that allow the finger portions 22 to separate from the palm portion 20 of the temporary expandable layer 18, e.g., by applying a sufficient force.

Figure 3:
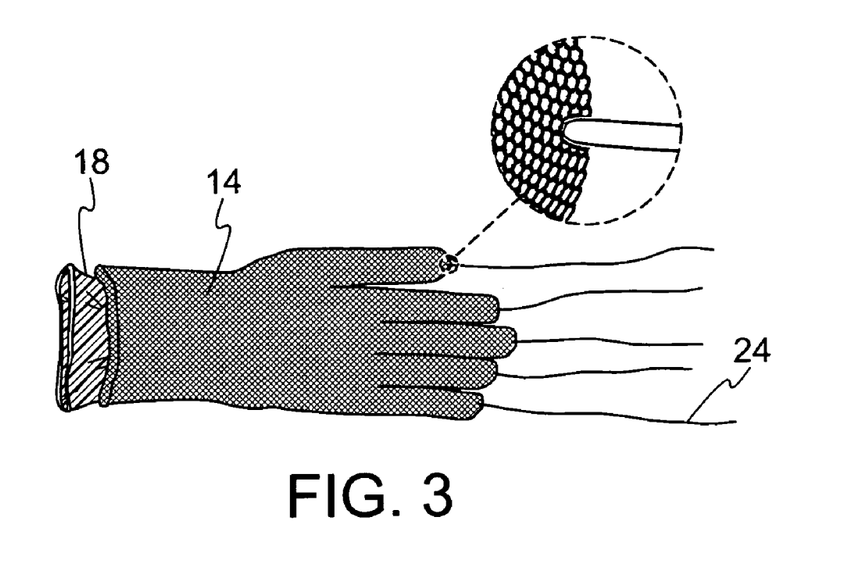
FIG. 3 illustrates the temporary expandable layer inserted into the power layer of FIG. 2 such that cords of the temporary expandable layer pass through mesh finger tip portions of the power layer.

As noted in greater detail herein, the power layer 14 of the mechanical counter pressure glove 10 comprises a mesh of elastic cloth. The elastic cloth is formed from a network of threads that define variable sized openings between threads of the elastic fabric. Referring to FIGS. 2 and 3, the temporary expandable layer 18 is inserted into the power layer 14 and the cords 24 that attach to each finger portion 22 of the temporary expandable layer 18 are passed through the network of threads of the power layer 14. FIG. 3 further shows an exploded view of a portion of the thumb tip to illustrate that the fine mesh structure of the power layer 14 is locally distorted by the much larger cord 24, which passes through only one gap in the mesh of the power layer 14.

Referring back to FIG. 2, the techniques and concepts described herein for donning a glove e.g., the mechanical counter pressure glove 10, are readily adapted to donning arm, leg, foot and other components of the mechanical counter pressure suit. Moreover, the techniques and concepts herein are readily adapted or directly applicable to donning other types of tight fitting, stretchable garments. For example, a garment to be donned may be shaped into a form such as a sleeve, leg, or sock garment 15. Under this arrangement, a temporary expandable layer 19 is used to temporarily expand the garment 15. The temporary expandable layer 19 is similar in material and construction to the temporary expandable layer 18, except that the shape of the temporary expandable layer 19, for such applications, may resemble a simple blind tube, e.g., a generally tube shaped layer that is substantially sealed or closed at one end.

For example, where the garment 15 is intended for the arm or leg, the temporary expandable layer is simply slipped into the garment 15. Under this arrangement, the open end of the temporary expandable layer 19 may protrude from one end of the garment 15, and the closed end of the temporary expandable layer 19 may protrude from the opposite end of the garment 15. Where the garment 15 comprises a foot garment, e.g., a sock, the temporary expandable layer 19 may include one or more cords 24, which may be positioned for example, about the closed end of the tube shape, and weakened areas 26, which may be provided for example, between the cord(s) 24 and the open end of the tube shape. Under this arrangement, each cord 24 passes through a network of threads, for example, in the toe area of the sock in a manner similar to that illustrated for the case of the glove seen in detail in FIG. 3.

Figure 4:
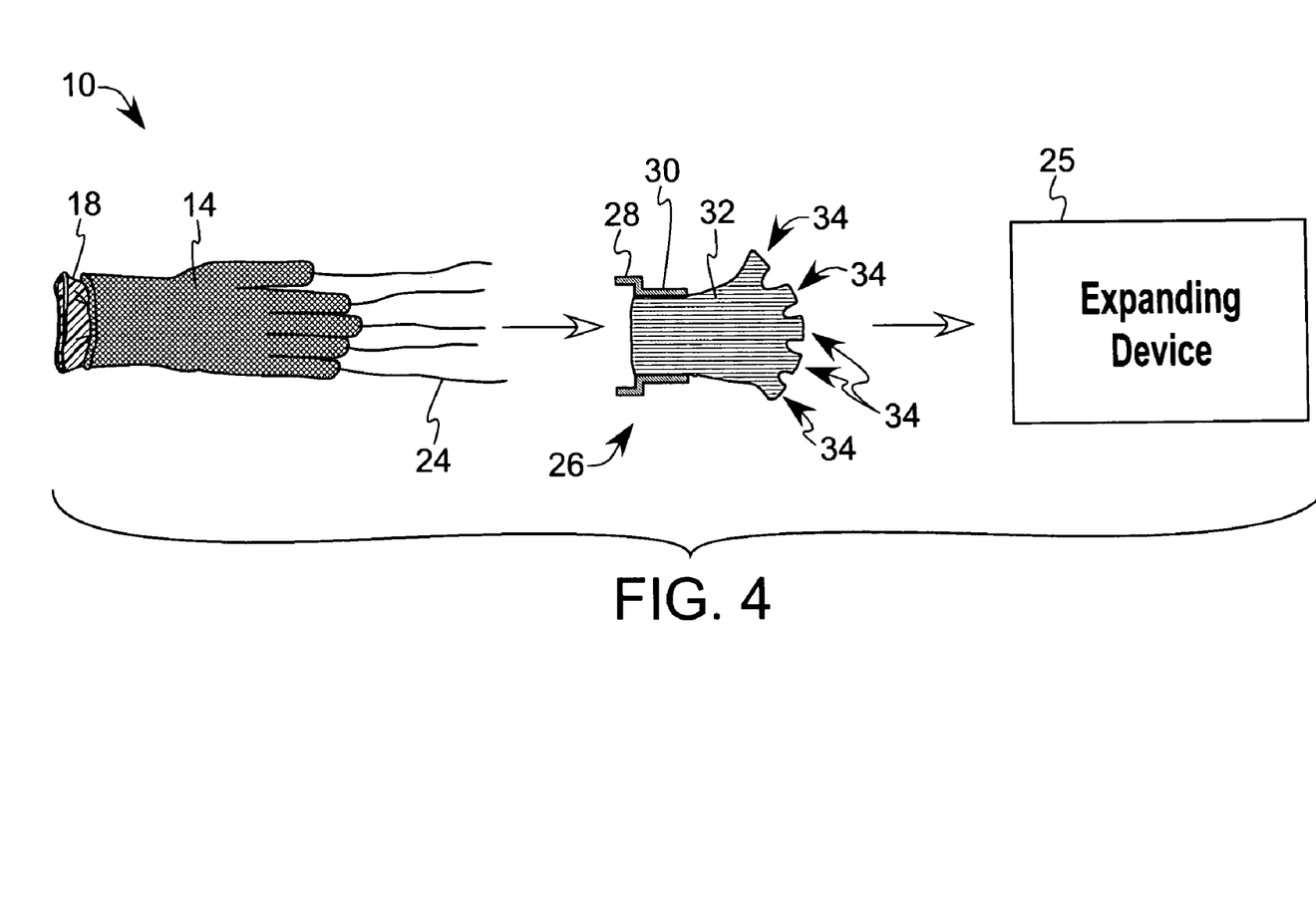
FIG. 4 illustrates an exemplary cuff and corresponding expanding device, e.g., a donning chamber, that may be used to expand the temporary expandable layer for donning the mechanical counter pressure glove of FIG. 2.

One aspect of the present invention is to ease the donning process by providing an apparatus that pre-stretches the garment to be donned. Once the garment is properly donned, the stretching force is released. The mechanical counter pressure glove 10 is one of the more difficult components of a mechanical pressure suit to don. As such, the donning of the glove 10 will be described in greater detail below. However, the techniques and methods are equally applicable to donning other garments including the garments 15 schematically illustrated in FIG. 2. Referring to FIG. 4, the power layer 14 may be expanded by the aid of an expanding device 25 and optionally, a corresponding cuff 26. As shown, the cuff 26 includes a flanged portion 28 and an extension portion 30. The power layer 14 and the temporary expandable layer 18 are passed through the cuff 26 and the temporary expandable layer is sealed about the flanged portion 28. The extension portion 30 is further inserted into or is otherwise attached to the expanding device 25 so as to form a seal therewith. Alternatively, the cuff 26 may be fixed to or integral with the expanding device 25.

The cuff 26 may also optionally include an expansion limiting device 32 that extends from the extension portion 30 opposite the flanged portion 28. For donning gloves, the expansion limiting device 32 may comprise a substantially non-stretchable structure that generally resembles an oversized palm portion that includes a plurality of apertures 34 for receiving the fingers of the power layer 14 therethrough. While optional, the expansion limiting device 32 may be used to prevent excessive expansion of one portion of the temporary expandable layer 18 relative to another portion. For example, the palm portion of the temporary expandable layer 18 may tend to over-expand relative to the associated finger portions. Thus the expansion limiting device 32 may be used to bound or limit an amount of expansion at least a portion of the temporary expandable layer 18.

Figure 5:
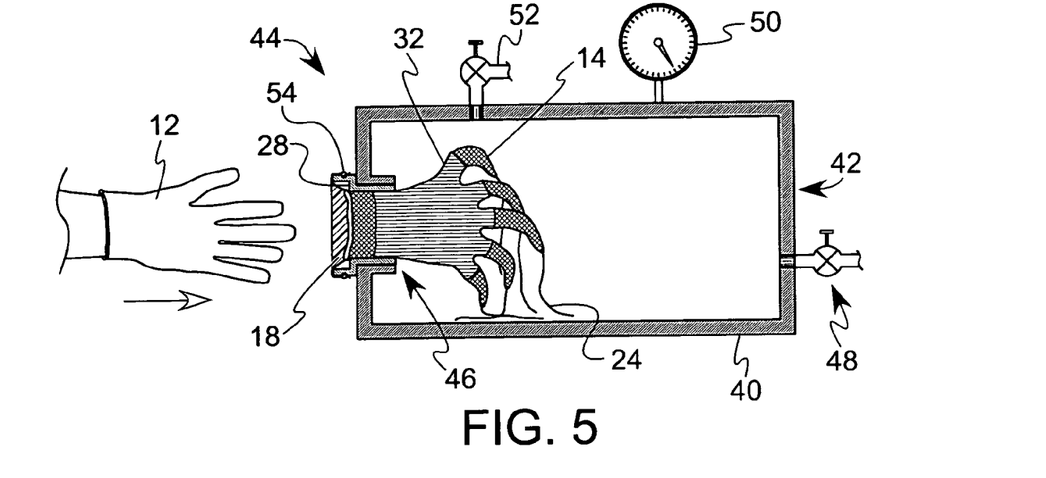
FIG. 5 illustrates a donning chamber where the cuff has been inserted into the chamber.

Referring to FIG. 5, a donning chamber 40 illustrates one exemplary manner of implementing the expanding device 25. The donning chamber 40 includes a first end 42 that is closed and a second end 44 opposite the first end 42, which includes an aperture 46 therethrough. The aperture 46 provides a port through which a hand may be inserted into the chamber to don the power layer 14. As will be seen, the cuff 26, or other sealing structure, preferably forms a tight seal about the periphery of the aperture 46 and holds the power layer 14 in place during the donning process.

Overall, the donning chamber 40 may be constructed in any reasonable manner so long as the donning chamber 40 is operable to briefly expand the temporary expandable layer 18 by an amount sufficient to assist the a user in donning an appropriate garment. For example, the donning chamber 40 may use negative pressure derived by forming at least a partial vacuum. In this regard, the donning chamber 40 may also include a valve connection 48 that is provided to a vacuum source (not shown), a pressure gauge 50 for displaying negative pressure, and an optional equalizer/relief valve 52.

The assembly discussed with reference to FIG. 4, which includes the power layer 14, the temporary expandable layer 18, the cuff 26, and optionally the expansion limiting device 32, are inserted into the aperture 46 of the donning chamber 40 and a seal is formed. For example, as shown in FIG. 5, the extension portion 30 of the cuff 26 forms a seal with the periphery of the aperture 46. The flanged portion 28 of the cuff is thus positioned proximate to the outer wall of the second end 44 of the donning chamber 40. A wrist portion of the temporary expandable layer 18, and optionally a wrist portion of the power layer 14, is folded over the flanged portion 28 of the cuff 26 and a retaining device 54 is used to seal the temporary expandable layer 18 to the cuff 26.

However it is contemplated that other sealing arrangements and methods may be utilized to form a seal with the donning chamber 40. For example, the cuff 26 may be integral with the donning chamber 40, or installed through the aperture 46 prior to inserting the power layer 14 through the expansion limiting device 32. Moreover, any reasonable chamber construction and sealing arrangement may be implemented so long as at least a partial vacuum or other source can be created that is sufficient to expand the temporary expandable layer 18 enough to assist in donning the power layer 14. The exact arrangement of the donning chamber 40 and any corresponding sealing arrangements will likely vary depending upon factors such as the garment to be donned, and the manner in which the expanding device is operated and/or powered. For example, to don a garment 15, e.g., for the leg or arm, the donning chamber 15 will likely need to be physically larger in size than that required to don the power layer 14 of the mechanical counter pressure glove 10.

Figure 6:
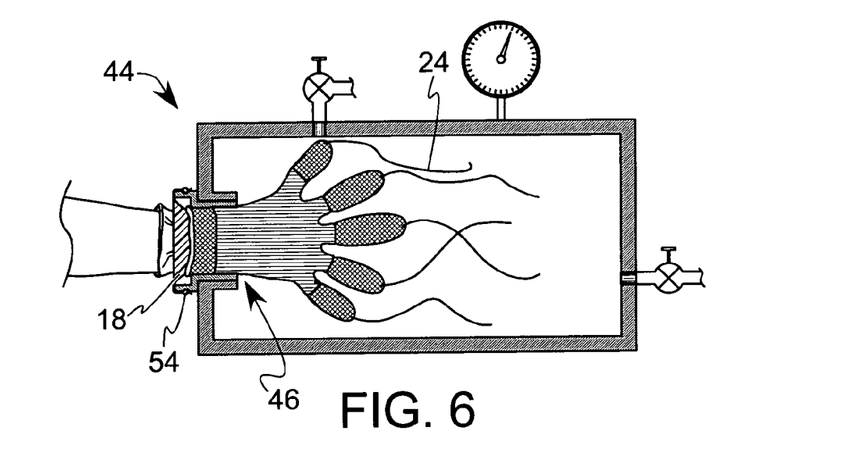
FIG. 6 illustrates the donning chamber of FIG. 5, where the temporary expandable layer is expanded, and a user has donned the mechanical counter pressure glove.

Referring to FIG. 6, once the cuff 26 is suitably sealed with respect to the aperture 46 in the donning chamber 40, and the temporary expandable layer 18 is suitably sealed with respect to the cuff 26, the donning chamber 40 is evacuated, e.g., to 220 to 240 mmHg below ambient, so that the temporary expandable layer 18 expands and pushes against the power layer 14, thereby expanding the power layer 14. The wearer, who has previously donned the comfort layer 12, inserts the appropriate hand into the donning chamber 40 through the cuff 26 and into the power layer 14. Once the hand is fitted in the power layer 14, the vacuum source is turned off and air is allowed to once again fill the donning chamber 40. As the donning chamber 40 fills with air, the power layer 14 will begin to press against the hand as it is intended to do.

The temporary expandable layer 18 may be undesirable except for the donning process. For example, the construction of the MCP suit allows natural thermoregulation as sweat may be evaporated by the vacuum of space through the mesh knitting of the comfort and power layers 12, 14 without the requirement of external cooling equipment. Thus, when working in space, over garments that may be worn for micrometeorite protection and for control of thermal radiation can be worn loose and unsealed to allow sweat to evaporate. However, the thermoregulation capability of the MCP suit may be inhibited by the nonporous nature of the temporary expandable layer 18 if left between the comfort layer 12 and the power layer 14.

Figure 7:
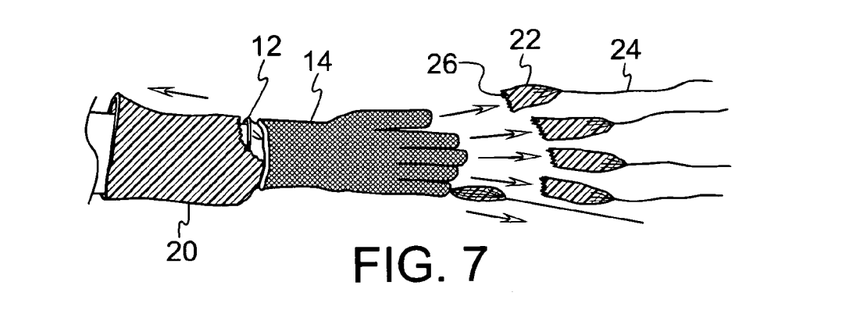
FIG. 7 illustrates a user removing the temporary expandable layer from underneath the power layer.

As such, it may be desirable to alter or remove the temporary expandable layer 18, at least partially, after donning the power layer 14. Referring to FIG. 7, to remove the temporary expandable layer 18 without removing the power layer 14, the cords 24 of the temporary expandable layer 18 are tugged. When pulled with sufficient force, the temporary expandable layer 18 is separated into two or more sections. For example, where the temporary expandable layer 18 is constructed as is shown in FIG. 2, the finger portions 22 may tear from the palm portion 20 about the weakened areas 26. Because of the porous nature of the mesh construction of the power layer 14, the finger portions 22 of the temporary expandable layer 18 pull through the power layer 14 from the inside out. Once the finger portions 22 are removed from underneath the power layer 14, the palm portion 20 of the temporary expandable layer 18 may be slipped over the wrist, up the arm and pulled out over the power layer 14.

Figure 8:
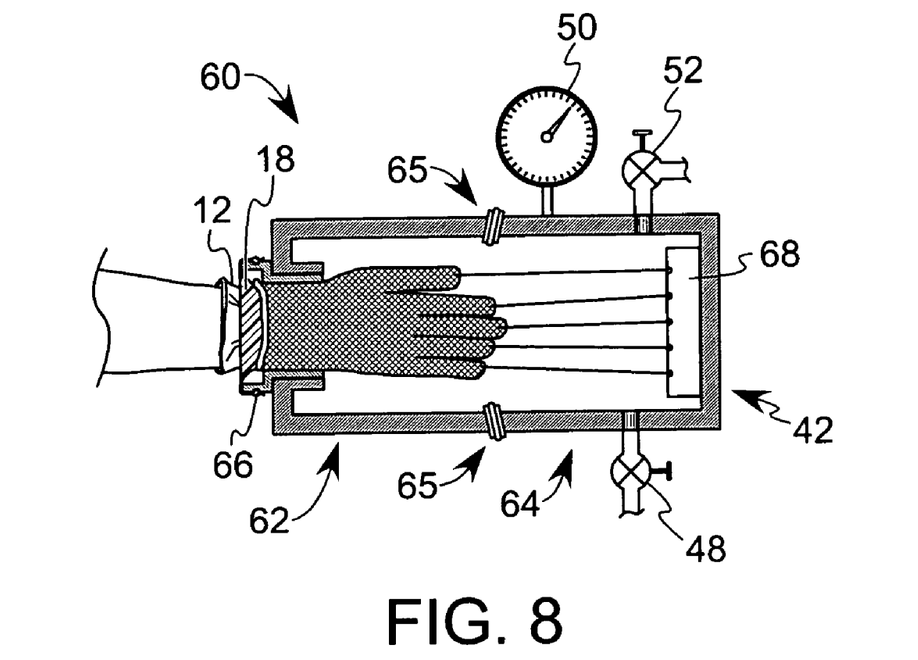
FIG. 8 illustrates an alternative exemplary donning chamber wherein the cords of the temporary expandable layer are connected to the a holder within the chamber for automatic removal of portions of the temporary expandable layer, e.g., when a hand of the wearer is withdrawn from the donning chamber.

Another exemplary technique to remove the temporary expandable layer 18 is described below with reference to FIG. 8. The donning chamber 60 is capable of forming a vacuum, and as such, the donning chamber includes many of the same features as the donning chamber 40 schematically illustrated in FIGS. 5-6. For example, the chamber 60 includes a suitable valve connection 48 that is provided to a vacuum source (not shown), a pressure gauge 50 for displaying negative pressure, and an optional equalizer/relief valve 52. The donning chamber 60 is however, provided as a first chamber portion 62 and a second chamber portion 64.

As shown, the first chamber portion 62 comprises approximately one half the length of the chamber 60, and the second chamber portion 64 comprises approximately the other half of the length of the chamber 60. However, other apportionments may easily be implemented. Also, the first and second chamber portions 62, 64 may be shaped differently from one another. For example, the first chamber portion 62 may take on a taper with respect to the second chamber portion 64. Under this arrangement, a cuff such as that discussed with reference to FIGS. 4-7 may be unnecessary where an outer periphery of the tapered portion of the first chamber portion 62 is used to retain the temporary expandable layer 18, such as by using a suitable retaining device to seal the temporary expandable layer 18 to the chamber 60 during donning of the power layer 14. The break between the first and second chamber portions 62, 64 may be sealed, such as with O-rings or other suitable sealing arrangements 65 when the chamber 60 is evacuated, or where the temporary expandable layer 18 is otherwise expanded. Further, the chamber 60 in FIG. 8 is illustrated without the expansion limiting device 32 to illustrate the optional nature of this component.

As noted above, the temporary expandable layer 18 is constructed of a nonporous layer, e.g., of a plastic film, and may include weakened areas 26, such as break lines, that are scored around the base of the finger portions 22, e.g., across the finger webs. The break lines are designed so as to not break while inserting a hand into the donning chamber 60, and thus the scores may be just strong enough to survive the entry of the subject's hand. The cords 24 of the temporary expandable layer 18 extend from each finger portion 22 of the temporary expandable layer 18, through the power layer 14, and connect to a suitable support structure 68 within the donning chamber 60.

The donning chamber 60 is evacuated, e.g., to 220 to 240 mmHg below ambient, so that the temporary expandable layer 18 expands and pushes against the power layer 14, thereby expanding the power layer 14. The subject dons the comfort layer 12 and inserts the hand into the pre-expanded power layer 14. Once the power layer 14 is sufficiently donned, the vacuum source is turned off and air is allowed to once again fill the donning chamber 60. As the donning chamber fills with air, the power layer 14 will begin to press against the subject as it is intended to do. Further, the equalization of pressure in the donning chamber 60 allows the first and second chamber portions 62, 64 of the donning chamber 60 to separate easily about the sealing O-rings 65.

After the power layer 14 is donned and after air has reentered the donning chamber 60, a backwards pull of the hand releases the first chamber portion 62 from the second chamber portion 64 about the sealing arrangement 65. As the hand is withdrawn from the chamber 60, the weakened areas 26 of the temporary expandable layer 18 tear or otherwise separate. However, the finger portions 22 of the temporary expandable layer 18 are secured to the chamber 60 by their associated cords 24 and the corresponding support structure 68. As such, the finger portions 22 of the temporary expandable layer 18 will pull through the mesh of the power layer 14 in a manner analogous to that described with reference to FIG. 7, and will be left behind with the donning chamber 60. The palm portion 20 of the temporary expandable layer 18 may then be pulled free at the wrist and discarded as described with reference to FIG. 7.

Figure 9:
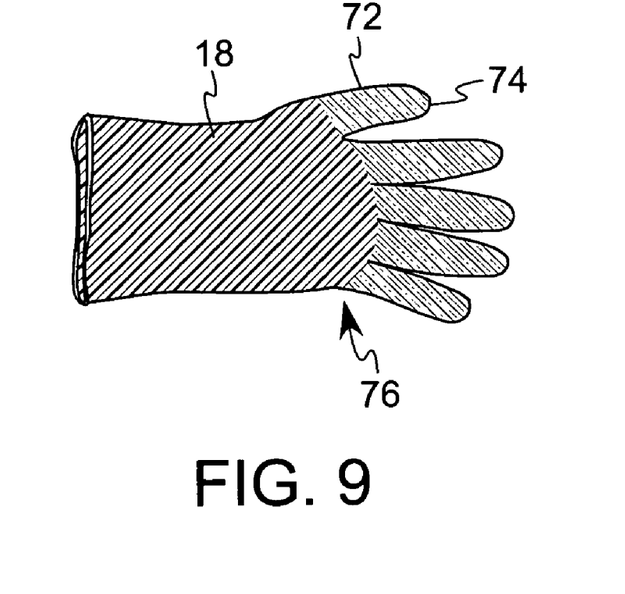
FIG. 9 is a schematic illustration of an expandable layer that comprises soluble or otherwise disintegratable sections.

As an alternative to pulling the temporary expandable layer 18 through the mesh of the power layer 14, the temporary expandable layer may be otherwise slipped out from under the garment or a chemical or physical treatment may be used to crumble, dissolve or disintegrate at least a portion of the temporary expandable layer 18. For example, referring to FIG. 9, the temporary expandable layer 18 may be constructed such that the finger tips 74 and finger webs 76 are constructed from a water-soluble material and the remainder of the temporary expandable layer 18 comprises a heavy plastic material. Under this arrangement, any reasonable donning chamber construction may be used to first expand the temporary expandable layer 18 by an amount sufficient to assist donning the power layer 14 as described in greater detail herein. To remove, at least partially, the temporary expandable layer 18 from underneath the power layer 14, the water-soluble portions of the temporary expandable layer 18 are wetted, e.g., using a sponge, and the remaining insoluble portions are extracted, e.g., from the wrist. Other solvent-based techniques may alternatively be used. Further, physical means, e.g., ultrasound or ultraviolet radiation, may be used to crumble or disintegrate a portion or the entire temporary expandable layer 18, leaving a residue of granules that will be discarded after the glove is doffed. This residue will permit the evaporation of sweat through the mesh of the power layer as previously mentioned herein.

The donning chambers 40, 60 may also be used to don other garments including for example, the garment 15, e.g., an arm, leg or foot garment schematically illustrated in FIG. 2. Under this arrangement, the temporary expandable layer 19 is inserted into the garment 15 and both are passed through the cuff 26. The open end of the temporary expandable layer 19 is sealed about the flange 28 of the cuff 26 using the retaining device 54, and a vacuum is drawn in the donning chamber 40, 60 as described in greater detail herein. After the temporary expandable layer 19 has stretched the garment 15 and the garment has been at least substantially donned, air replaces the vacuum so that the garment 15 presses on the corresponding body part. The temporary expandable layer 19 is removed from underneath the garment 15, e.g., by pulling on the protruding blind end of the temporary expandable layer 19 in the case of an arm or leg garment, or by pulling the cord 24 in the case of a sock or other similar garment for the foot. Further, the temporary expandable layer 19 may be crumbled, dissolved or otherwise disintegrated in a manner analogous to that described more fully herein.

Moreover, although described with reference to a mechanical counter pressure garment, the systems, apparatuses and methods herein may be applied to donning other garments including pressure, compression and support garments.

Having described the invention in detail and by reference to preferred embodiments thereof, it will be apparent that modifications and variations are possible without departing from the scope of the invention defined in the appended claims.

What is claimed is:

1. A method of donning a garment comprising:
inserting an expandable layer into a support garment to be donned, said expandable layer sufficiently gas tight to expand said support garment;
inserting said garment and expandable layer into a donning chamber having a vacuum source;
utilizing said vacuum source to draw a sufficient vacuum within said donning chamber so as to expand said expandable layer and said garment so that said garment pre-stretches by a sufficient amount to assist in the donning of said garment;
donning said expandable layer and said garment after said garment has been pre-stretched and while said garment remains expanded by said vacuum source;
evacuating the vacuum from said donning chamber;
removing the donned garment from said donning chamber; and
removing at least a portion of said expandable layer from underneath said garment after said garment has been donned without removing said garment, wherein said garment applies intended pressure to a subject.

2. The method according to claim 1, wherein removing at least a portion of said expandable layer comprises pulling at least a portion of said expandable layer through an opening in said garment.

3. The method according to claim 1, wherein:
at least a portion of said garment comprises a mesh; and
removing at least a portion of said expandable layer comprises pulling at least a portion of said expandable layer through said mesh.

4. The method according to claim 3, wherein:
said expandable layer comprises at least one cord extending from a portion thereof;
inserting said expandable layer into said garment further comprises passing at least one cord of said expandable layer through said mesh in said garment; and
removing at least a portion of said expandable layer comprises pulling each cord so as to remove at least a portion of said expandable layer through said mesh.

5. The method according to claim 1, wherein said expandable layer comprises at least one weakened area and removing at least a portion of said expandable layer comprises separating said expandable layer about said weakened area.

6. The method according to claim 1, wherein removing at least a portion of said expandable layer comprises at least one of dissolving, crumbling or disintegrating at least a portion of said expandable layer underneath said garment.

7. The method according to claim 1, wherein:
said garment comprises a glove; and
said expandable layer comprises a generally glove shaped nonporous material.

8. The method according to claim 1, wherein:
said garment comprises at least one of an arm, leg or foot garment; and
said expandable layer is shaped generally as a blind tube of nonporous material.

9. A system for donning a garment comprising:
a temporary expandable layer that is insertable into a support garment to be donned, said expandable layer sufficiently gas tight to expand said support garment;
a donning chamber in which to insert said garment and expandable layer;
a vacuum source coupled to said donning chamber which is configured such that when said garment and temporary expandable layer are inserted in said donning chamber and a vacuum is applied to said donning chamber by said vacuum source, said temporary expandable layer and said garment pre-stretch so as to assist a user in donning said temporary expandable layer and said garment after they have been pre-stretched; and
a means for removing said temporary expandable layer without removing said garment;
wherein said garment applies intended pressure to a subject that donned the garment.

10. The system according to claim 9, wherein:
said temporary expandable layer comprises at least one weakened area; and
said means for removing said temporary expandable layer comprises at least one cord extending from said temporary expandable layer, each cord arranged such that pulling thereof causes said expandable layer to separate into two or more portions about at least one weakened area.

11. The system according to claim 9, wherein said system comprises a system for donning gloves, wherein:
said temporary expandable layer comprises:
a palm portion;
a plurality of finger portions;
a weakened area generally between each of said finger portions and said palm portion; and
said means for removing said temporary expandable layer comprises a cord extending from each finger portion, each cord arranged such that pulling thereon causes said temporary expandable layer to separate about a corresponding weakened area.

12. The system according to claim 9, wherein:
said expandable layer comprises at least one portion comprising a soluble material that is dissolvable from underneath said garment; and
said means for removing said temporary expandable layer comprises a corresponding solvent that is applied to at least a portion of said soluble material.

13. The system according to claim 9, wherein:
said expandable layer comprises at least one portion comprising a material that may be at least partially crumbled or disintegrated from underneath said garment; and
said means for removing said temporary expandable layer comprises a corresponding physical treatment for crumbling or disintegrating said material.

14. The system according to claim 9, wherein:
said garment comprises a glove; and
said expandable layer comprises a generally glove shaped nonporous material.

15. The system according to claim 9, wherein:
said garment comprises at least one of an arm, leg or foot garment; and
said expandable layer is shaped generally as a blind tube of nonporous material.

16. An expandable layer for donning a garment comprising:
an expandable layer that is sufficiently gas tight to expand a corresponding support garment having:
a first portion;
a second portion;
a weakened area between said first and second portions; and
at least one cord extending from said second portion;

wherein said garment may be slipped over said expandable layer and said expandable layer may be expanded in a donning chamber by drawing a vacuum at least for a period of time sufficient to pre-stretch said expandable layer and said garment before a subject dons said garment;

wherein said cord may be pulled after said garment has been donned by a sufficient amount to separate said first portion of said expandable layer from said second portion of said expandable layer such that at least a portion of said expandable layer is removed from underneath the donned garment.

17. The expandable layer according to claim 16, wherein:
said expandable layer comprises a glove,
said first portion comprises a palm portion;
said second portion comprises a plurality of finger portions;
said weakened areas comprise a perforation that divides each finger portion from said palm portion; and
said at least one cord comprises a cord extending from each finger portion.

18. The expandable layer according to claim 16, wherein:
said garment comprises at least one of an arm, leg or foot garment; and
said expandable layer is shaped generally as a blind tube of nonporous material.

* * * * *